US006566543B2

(12) United States Patent
Mechoulam et al.

(10) Patent No.: US 6,566,543 B2
(45) Date of Patent: May 20, 2003

(54) 2-ARACHIDONYLGLYCEROL (2-AG)-AN INHIBITOR OF TUMOR NECROSIS FACTOR-α AND NEUROPROTECTOR OF BRAIN IN CLOSED HEAD INJURY

(75) Inventors: Raphael Mechoulam, Jerusalem (IL); Ruth Gallily, Jerusalem (IL); Aviva Breuer, Jerusalem (IL); Esther Shohami, Mevasseret Zion (IL); David Panikashvili, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 13 days.

(21) Appl. No.: 09/887,745

(22) Filed: Jun. 22, 2001

(65) Prior Publication Data

US 2002/0072539 A1 Jun. 13, 2002

Related U.S. Application Data

(60) Provisional application No. 60/213,705, filed on Jun. 23, 2000.

(51) Int. Cl.[7] .............................................. C07C 57/00
(52) U.S. Cl. ....................................... 554/227; 514/552
(58) Field of Search ........................... 554/227; 514/552

(56) References Cited

U.S. PATENT DOCUMENTS 5,456,912 A 10/1995 German et al. .......... 414/195.1

FOREIGN PATENT DOCUMENTS

| | | |
|---|---|---|
| EP | 0505817 | 9/1992 |
| WO | 9951560 | 10/1999 |

OTHER PUBLICATIONS

Di Marzo, V. et al: Cannabimimetic Fatty Acid Derivatives in Cancer and Inflammation; Prostaglandins and Other Lipid Mediators, vol. 61, Nos. 1–2, pp. 43–61, XP004197447.

Sinor, A.D. et al.: "Endocannabinoids Protect Cerebral Cortical Neurons From In Vitro Ischemia in Rats"; Neuroscience Letters, vol. 278, No. 3, Jan. 14, 2000; pp. 157–160, XP002205898.

*Primary Examiner*—Deborah D. Carr
(74) *Attorney, Agent, or Firm*—Steinberg & Raskin, P.C.

(57) ABSTRACT

The present invention relates to 2-arachidonylglycerol (2-AG) to be used as inhibitor of a tumor necrosis factor (TNF-α), in the reduction of edema caused by closed head injury, in the reduction of neurological deficits caused by closed head injury and stroke and in treating pathological conditions caused by TNF-α and/or by radical oxygen intermediates (ROI), in pharmaceutical composition for the same use comprising as active ingredient 2-AG. It comprises also the use of 2-AG and pharmaceutical compositions comprising same in the preparation of a medicament for the treatment of said indications and methods of treatment by 2-AG and pharmaceutical compositions comprising same for diseases caused by said indications.

8 Claims, 3 Drawing Sheets

2-ARACHIDONYLGLYCEROL (2-AG)-AN INHIBITOR OF TUMOR NECROSIS FACTOR-α AND NEUROPROTECTOR OF BRAIN IN CLOSED HEAD INJURY

This application claims the benefit of Provisional application Ser. No. 06/213,705, filed Jun. 23, 2000.

FIELD OF THE INVENTION

1. The present invention relates to 2-arachidonylglycerol (2-AG) to be used as inhibitor of a tumor necrosis factor (TNF-α), in the reduction of edema caused by closed head injury, in the reduction of neurological deficits caused by closed head injury and stroke and in treating pathological conditions caused by TNF-α and/or by radical oxgen intermediates (ROI), in pharmaceutical composition for the same use comprising as active ingredient 2-AG, the use of 2-AG and pharmaceutical compositions comprising same in the preparation of a medicament for the treatment of said indications and methods of treatment by 2-AG and pharmaceutical compositions comprising same for diseases caused by said indications.

BACKGROUND OF THE INVENTION

2. Two types of endogenous cannabinoids have been identified, the most thoroughly investigated compounds being arachidonylethanolamide (anandamide) and 2-arachidonylglycerol (2-AG) (Mechoulam and Ben-shabat, 1999). Although these endocannabinoids, in particular anandamide, have been the object of investigations in various systems, their physiological roles are not clear (Mechoulam et al., 1998). In view of the anti-inflammatory action of plant and synthetic cannabinoids, and of the presence of endocannabinoids and of cannabinoid receptors in organs associated with immune regulation, a plausible role attributed to the endocannabinoid system is an anti-inflammatory one. Indeed, anandamide has been shown to exhibit anti-inflammatory effects (Molina-Holgado et al., 1997) and 2-AG suppresses interleukin-2 through down regulation of the nuclear factor of activated T cells (Ouyang et al., 1998).

3. Tumor necrosis factor-α (TNF-α) is involved in the pathogenesis of various immune mediated processes and is the key mediator in septic shock (Tracey and Cerami 1993). This cytokine is released mainly by mononuclear phagocytic cells in response to injection of lipoplysaccharide (LPS, an endotoxin derived from Gram negative bacteria) to experimental animals. TNF-α affects both the central nervous system and periphery. It causes fever, sickness behavior, anorexia, symphathetic discharge and stimulation of pituitary hormones. It can also induce programmed cell death in neurons.

4. Circulating TNF-α and other cytokines have been, shown to be transported into the brain and to affect its function. TNF-α can be synthesized in the brain in situ, mainly by microglia, but also by astrocytes, neurons and endothelial cells. TNF-α activity can be induced by ischemic and traumatic brain injury (Newton and Decicco, 1999 and ref. cited) and it plays a dual role in the pathophsiology of these injuries (shohami et al. 1999).

5. Since TNF-α is an important inflammatory mediator, inhibition of its production by a body constiuent may reflect a role for such an endogenous ligand in the anti-inflammatory processes of a living tissue. We now report that 2-AG inhibits in vitro TNF-α production both in-vitro, in murine macrophages, as well as in mice.

6. As cannabinoids have been shown to have antioxidative properties (Mechoulam et al., 1998) we also looked into the action of 2-AG on the formation of radical oxygen intermediates (ROI). These are highly toxic species that are formed in many biological reactions.

7. We investigated the effect of various concentrations of 2-AG (0.05–50 μg/ml) on the production of TNF-α and nitric oxide generation by macrophages. These cells were chosen on the basis of their versatility, as they participate very actively in innate and immune functions. They phagocytize, ingest and destroy many infections agents, and act as effector cells in both humor and cell mediated immune responses. However, macrophages can also cause a wide array of inflammatory diseases.

8. Mouse peritoneal macrophages (harvested from C57BL/6 mice) were incubated in vitro with various concentrations of 2-AG, together with either LPS, which triggers TNF-α production, or with LPS and IFNγ, which together trigger nitric oxide generation. In the concentration studied (50 μg/ml–0.5 μg/ml) 2-AG was not toxic to macrophages assessed either by trypan blue or erythosin B dye exclusion. TNF-α production was determined by bioassay using BALB/c CL.7 cells as targets (Gallily et al., 1997).

9. ROI formation in macrophages was determined by a luminol-enhanced chemiluminescence response assay (employing biolumate LB 85, Belhold, Wildbad, Germany (Avron and Gallily, 1995).

10. For determination of the effect of 2-AG on TNF-α levels in serum of LPS-treated mice, female C57BL/6 mice 9–11 weeks old, weighing 20–23 gr were injected i.p. with either 5 mg/kg LPS alone or with LPS (5 mg/kg) and 2-AG (10 mg/kg) or with LPS (5 mg/kg) and 2-AG (1 mg/kg) 2-linoleoylglycerol (2-LinoG) (10 mg/kg) and 2-palmitoylglycerol (2-PalmG) (5 mg/kg). After 90 min they were bled and serum TNF-α activity (titer) was bioassayed, as described above.

BRIEF DESCRIPTION OF THE DRAWINGS

11. The results of the tests performed in support of the statements made herein are given in the annexed drawings in which:

FIG. 1: show the inhibition of TNF-α and ROI production by 2-AG. Thioglycollate-elictied peritoneal macrophaqes were harvested from C57BL/6 mice. After overnight incubation the cells were treated with 2-AG.

DETAILED DESCRIPTION OF THE INVENTION

Figure 1A:
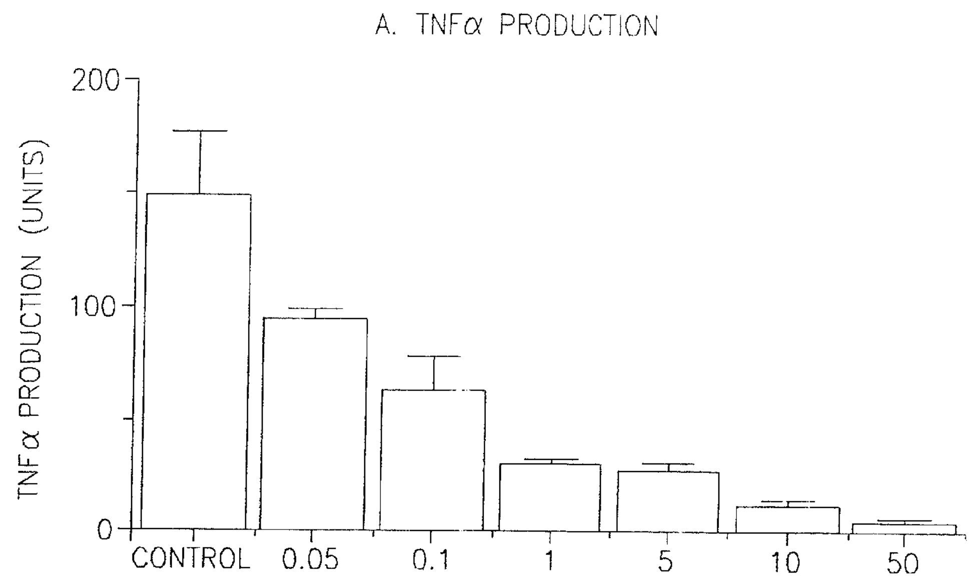
FIG. 1A shows 2-AG at concentration of 0.05–5 μg/ml were added together with 1 pg/ml LPS to the cells. Supernatants were harvested after 24 h for TNF-α determination by bioassay. The TNF-α titer is expressed in $S_{50}$ units, defined as the reciprocal of the test sample dilution required to destroy 50% of a CL.7 targent cell monolayer. A representative experiment of 5 assays carried on in tetraaplicates is shown on the curve. The differences were all significant ($p<0.05$, Mann-Whitny U-test). The values shown on the abscissa were obtained with LPS (1 μg/ml) and 2-AG (in μg/ml as indicated on the Figure).

12. As shown in FIG. 1A, a dose response TNF-α inhibition by 2-AG is noted in vitro. At concentrations of 50 and 10 μg/ml inhibition of 97% and 90% respectively was observed. Even at concentrations of 0.1 μg/ml 2-AG, 50% inhibition of μg/ml production was still noted. On the other hand, addition of 2-AG at the concentrations, i.e. 50 μg/ml–0.05 μg/ml to macrophage cultures by both LPS and IFNγ, did not suppress nitric oxide generation. This was determined on the basis of the accumulated nitrite in the supernatants of the treated macrophages using Griess reagent (data not shown).

Figure 1B:
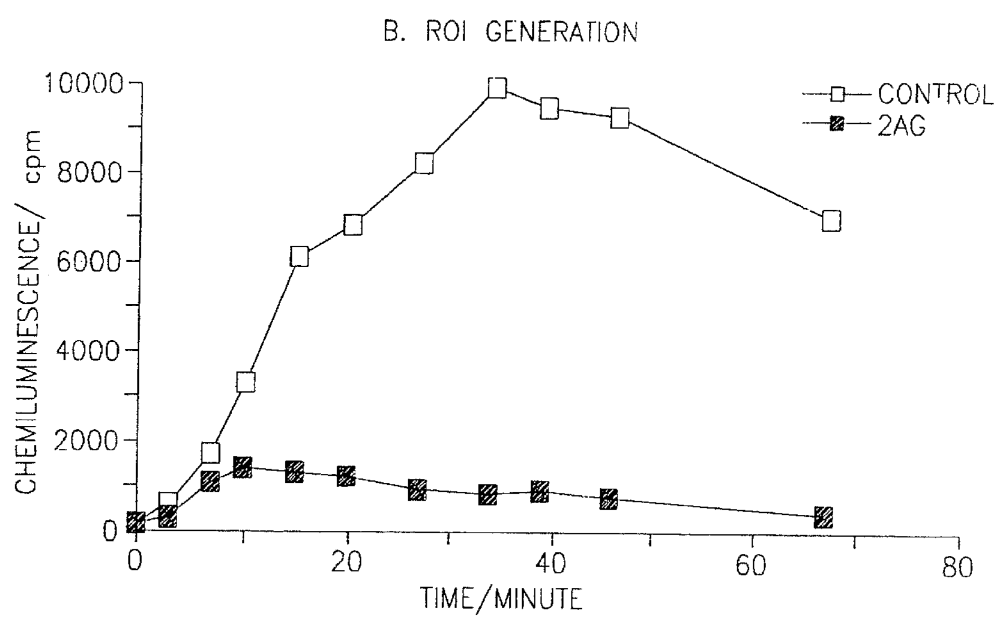
FIG. 1B shows Macrophages were incubated over night in chemiluminescence tubes, then washed and incubated with 25 pg/ml 2-AG luminol and zymusan. Chemiluminescence was recorded over 65 min.

13. Treatment of macrophages with 25 pg/ml 2-AG suppressed the production of Zymosan-induced ROI by more than 85% after 40 min as assessed by chemiluminescence (FIG. 1B)

14. Inhibition of TNF-α production was also seen in mice (Table 1).

TABLE 1

SUPPRESION OF In vivo TNF-α PRODUCTION BY 2-AG

| Group No. | No. of Mice | Agent | Dose (mg/kg) | TNFα titer Mean $S_{50}$ | TNFα titer % inhibition |
|---|---|---|---|---|---|
| 1 | 5 | 2-AG | 10 | 437 | 73 |
| | | LPS | 5 | | |
| 2 | 4 | 2-AG | 1 | 83 | 95 |
| | | 2-LinoG | 10 | | |
| | | 2-PalmG | 5 | | |
| | | LPS | 5 | | |
| 3 | 6 | LPS | 5 | 1633 | 0 |

15. Three groups of Female C57BL/6 mice were injected (i.p.)with either LPS alone (group 3), or with 2-AG and LPS (group 1)or with a mixture of 2-AG, 2-PalmG, 2-LinoG and LPS (group 2) at doses indicated in the Table.

16. When 2-AG (10 mg/kg) was administered together with LPS, 73% inhibition of TNF-α was observed. Co-administration of LPS with AG (1 mg/kg), 2-LinoG (10 mg/kg) and 2-PalmG (5 mg/kg) inhibited TNF-α production in 4 out of 5 mice almost totally (95%). We have previously shown that 2-LinoG and 2-PalmG, which accompany 2-AG in the body, although inactive in numerous in vivo and in vitro assays (including binding to the cannabinoid receptors), enhance 2-AG activity (Ben-Shabat et al., 1998). This enhancement, which we have named "entourage effect" is also seen here. 2-AG (1 mg/kg) in the presence of the "entourage" compounds, was more active than a considerably higher dose of 2-AG, namely 10 mg/kg (Table 1).

17. Various cannabinoids, both plant derived and synthetic, have been shown to reduce the production of inflammatory cytokines and nitric oxide. Anandamide also inhibits TNF-α production (in astrocytes), however, its effect is relatively modest (Molina-Holgado et al., 1997). Contrary to the results reported now with on the effect of 2-AG on macrophages; anandamide also blocked nitric oxide release in astrocytes.

18. As brain injury is associated with inflammatory processes we decided to look into the possibility that 2-AG may be a neuroprotective agent. We have seen that the production of 2-AG in brain is enhanced after closed head injury. This observation may possibly mean that the release of 2-AG is part of the brain's endogenous neuroprotectant mechanism.

19. One of the manifestations of brain injury is neuronal cell death that is grossly evidenced by an infarct around the site of injury. Mice were treated with either 2-AG (5 mg/kg) or vehicle, decapitated 24 hours later and their brains were examined for changes in infarct volume. Infarct volume was reduced in 2-AG treated mice, compared to that in vehicle treated mice (5.6±1.2% versus 9.9±1.6% respectively of total brain volume; p=0.053). No infarct was observed in sham operated rats (data not shown).

20. We tested the effect of 2-AG in an animal model of closed head injury (CHI) which has been developed in our laboratory (Chen et al. 1996). In this model, which mimics many of the clinical features of clinical head injury, edema formation and impairment of motor functions are among the typical disabling effects of the trauma. We therefore tested the effect of treatment with 2-AG on these two parameters after CHI.

21. Mice were subjected to CHI under ether anesthesia, using our weight-drop device, and the severity of injury was assessed using the Neurological Severity Score (NSS). Motor function and reflexes of the injured mice were also evaluated at 24 h after CHI. One point was awarded for the lack of a tested reflex or for the inability to perform the tasks. An accumulated scoring method was applied so that the NSS could range from 0 (successfully performing all the tasks) to 10 (failure in all the tasks). The series of tasks have been described in detail in previous publications (Chen et al. 1996) and recently modified to include only 10 different measurements, as shown in Table 2.

TABLE 2

Neurological Severity for head injured mice

| TASK | NSS |
|---|---|
| Presence of mono- or hemiparesis | 1 |
| Inability to walk on a 3 cm wide beam | 1 |
| Inability to walk on a 2 cm wide beam | 1 |
| Inability to walk on a 1 cm wide beam | 1 |
| Inability to balance on a 1 cm wide beam | 1 |
| Inability to balance on a round stick (0.5 cm wide) | 1 |
| Failoure to exit a 30 cm. diameter circle (for 2 min) | 1 |
| Inability to walk straight | 1 |
| Loss of startle behavior | 1 |
| Loss of seeking behavior | 1 |
| MAXIMUM TOTAL | 10 |

22. One point is awarded for failure to perform a task. NSS at 1 h in the range of 7–10: severe CHI 23. Neurological Severity Score A set of functional tests which is the basis for evaluation of the clinical status of a mice, after CHI. A point is awarded for failure to perform a task. The higher the score, the more severe is the injury.

24. We measured the NSS scores of the injured animals 1 hour and 24 hours after injury, and the differences between these values represent recovery. At 24 h post CHI, mice were decapitated, their brains removed and edema was evaluated by measuring the tissue water content, using the wet to dry weight ratio: $\%H_2O=[(WW-DW)\times 100]/WW$. 2-AG treatment was given either at 15 min or 1 h post CHI, at three doses (1, 5 and 10 mg/kg) and control mice were injected with the vehicle, at the same time points. Drug was injected either sub-cutaneously (s.c.) or intravenously (i.v.)

Figure 2:
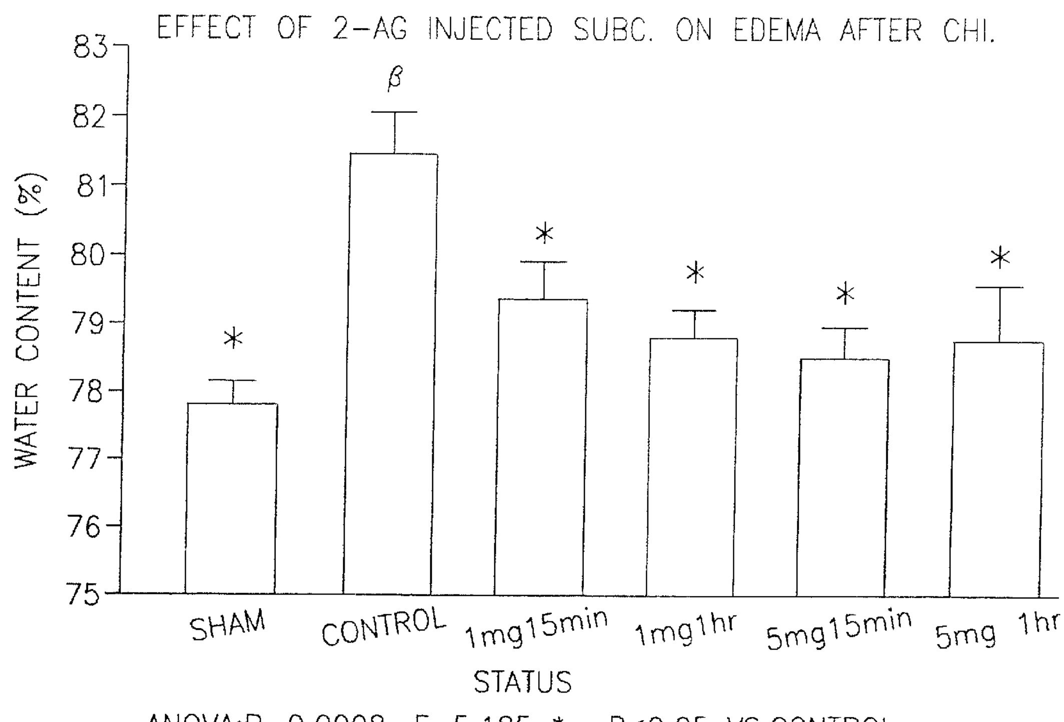
FIG. 2: shows the effect of 2-AG on edema formation after CHI. 2-AG at 1 or 5 mg/kg was injected s.c. to mice at 15 min or 1 h after CHI. Edema was evaluated at 24 h as percent tissue water content.
Figure 3:
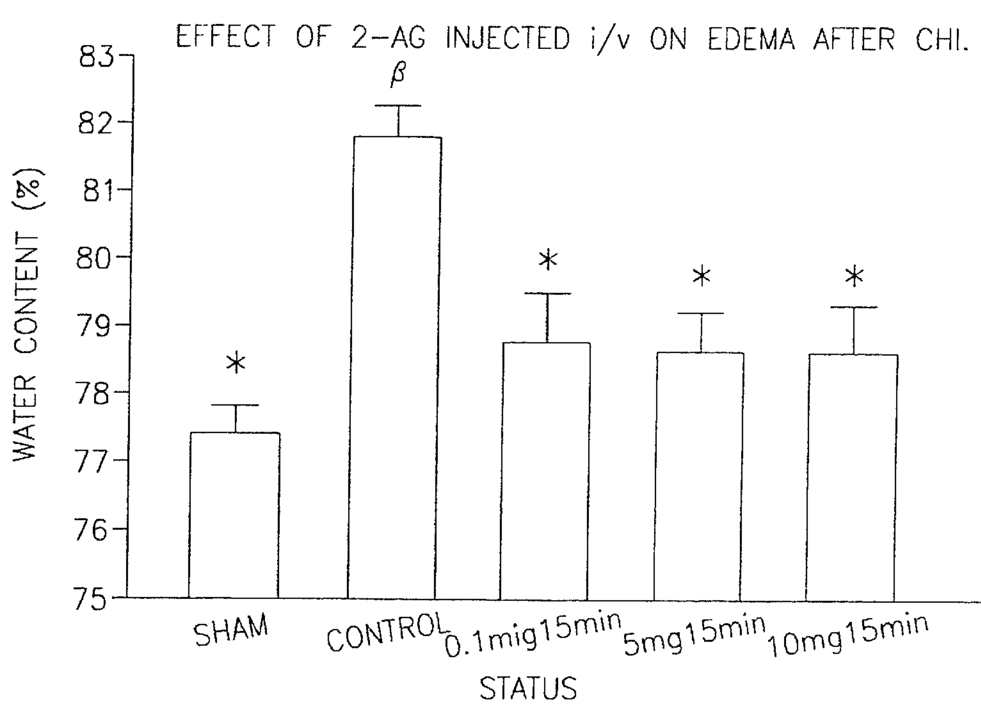
FIG. 3: shows the Effect of 2-AG on edema formation after CHI. 2-AG at 0/1, 5 or 10 mg/kg was injected i.v. to mice at 15 min after CHI. Edema was evaluated at 24 h as percent tissue water content.
Figure 4:
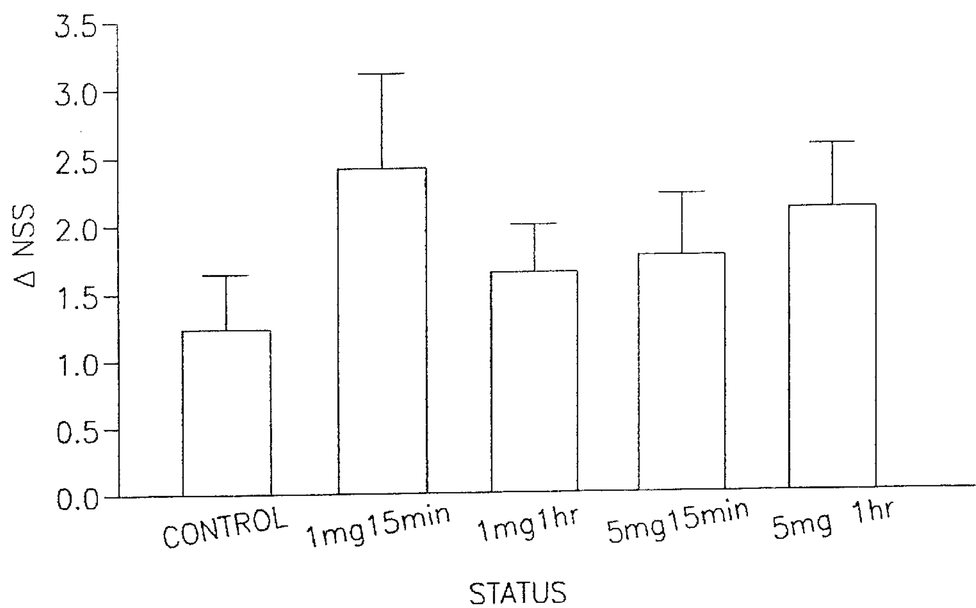
FIG. 4: shows the effect of 2-AG on clinical recovery after CHI. 2-AG at 1 or 5 mg/kg was injected to mice at 15 min or 1 h after CHI.. Clinical status was evaluated at 1 h and 24 h using the Neurological Severity Score. Recovery is expressed as: ΔNSS=NSS 1 h-NSS 24 h
Figure 5:
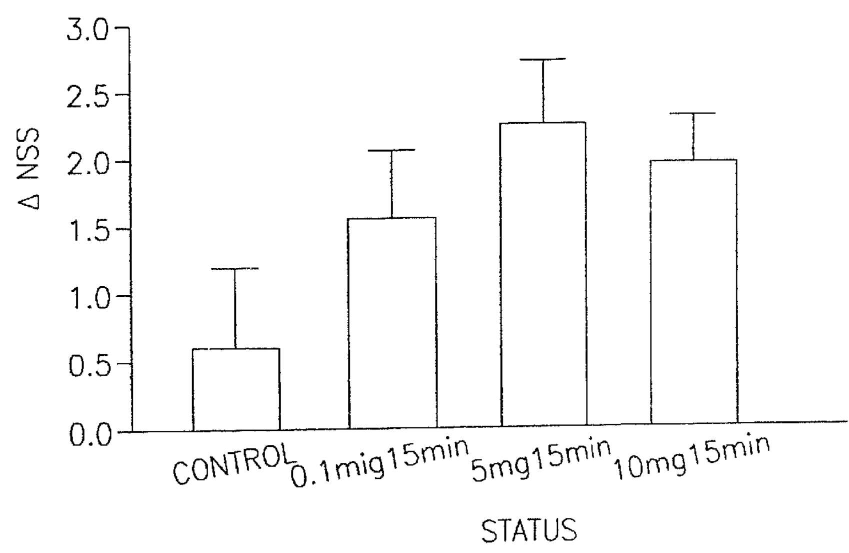
FIG. 5: shows the effect of 2-AG on clinical recovery after CHI. 2-AG at 0.1, 5 or 10 mg/kg was injected i.v. to mice at 15 min after CHI. Recovery was evaluated as described in FIG. 4.

25. We found that 2-AG (at a dose of 1 mg/kg and 5 mg/kg, but not at 10 mg/kg) reduced the edema significantly as compared to controls (FIGS. 2 and 3) when injected at 15 minutes or 1 hour post CHI. This effect was more pronounced after i.v. injection compared to s.c. injection. We also found that administration of 2-AG significantly improved the clinical recovery (based on the NSS score). Again i.v. administration led to better recovery than s.c. administration (FIGS. 4 and 5). Administration of 2-AG (1 mg)together with 2-LinoG (10 mg/kg) and 2-PalmG (5 mg/kg) enhanced potency almost 2-fold when compared to 2-AG (1 mg/kg) alone.

26. As many of the pathophysiological mechanisms of CHI are similar to those observed after stroke, it is reasonable to expect that 2-AG will also be active in this condition.

27. The present report is the first one that records the effect of the endogenous brain and peripheral constituent 2-AG on TNF-α. 2-AG, which is not toxic to macrophages up to a dose of 50 μg/ml was found to inhibit TNF-α formation. 2-AG also suppresses TNF-α production in vivo. Reduction of ROI production by macrophages was also noted. We also found that 2-AG administration reduces the edema and improves the clinical recovery of mice that have undergone closed head injury.

28. The compositions of the present invention are particularly effective in alleviating and even preventing neurotoxicity due to acute injuries to the central nervous system (CNS), such as injuries due to prolonged seizures, compromised or reduced blood supply, deprivation of glucose supply and mechanical trauma. The present compositions are also effective in alleviating other damages to the CNS like poison-induced convulsions, considered to be associated with amino acid receptors.

29. The compositions of the present invention may also be effective in the treatment of certain chronic degenerative diseases which are characterized by gradual selective neuronal loss. In this connection, the compositions of the present invention are contemplated as therapeutically effective in the treatment of Alzheimer's disease.

30. The present compositions are of special value in grand mal seizures, global hypoxic ischemic insults, in hypoxia, alone or in combination with blood reduction (ischemia), as well as in cases of cardiac arrest and in cases of abrupt occlusion of cerebral arteries (stroke).

31. The present invention thus consists in 2-Arachidonylglycerol (2-AG) or in pharmaceutical. compositions comprising same as active ingredient to be used as inhibitor of a tumor necrosis factor (TNF-α), in the reduction of edema caused by closed head injury, in the reduction of neurological deficits caused by closed head injury and stroke and in treating pathological conditions caused by TNF-α and/or by radical oxygen intermediates (ROI).

32. The pharmaceutical composition according to the present invention may comprise as additional active compounds 2-linoleoylglycerol and/or 2-palmitoylglycerol.

33. The pharmaceutical composition according to the present invention may comprise additional pharmaceutical active compounds and/or suitable pharmaceutical acceptable carrier, solvent, diluents, solid. etc.

34. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral or administration or for injection, the term including sub-cutaneous, transdermal, intravenous, intratechal, etc. administration. The liquid compositions include aqueous solutions, flavoured syrups, aqueous or oil suspensions, flavoured emulsions with edible oils, as well as elixirs and similar pharmaceutical vehicles. In addition, the compositions of the present invention may be formed as aerosols, for intranasal and like administration.

35. The present invention also consists in a method for the treatment of the diseases caused by the above indications with 2-AG or with pharmaceutical compositions comprising same.

36. The active dose for humans is generally in the range of from 0.05 mg to about 50 mg per kg body weight, in regimen of 1–4 times a day.

37. The preferred range of dosage is from 1.0 mg to about 20 mg per kg body weight. However, it is evident to the man skilled in the art that dosages would be determined by the attending physician, according to the disease to be treated, method of administration, patients age, weight, counter indications and the like.

38. The present invention also consists in the use of 2-AG or of pharmaceutical compositions comprising same in the preparation of a medicament for the treatment of the above indications.

39. The present invention will now be illustrated by the following Examples without being limited by same:

EXAMPLE 1

Emulphor

40. Active agents according to the invention were dissolved in ethanol/Emulphor 620 (GAF, USA). Bidistilled water was added. Ratio of ethanol:Emulphor:water in final solution was 1:1:18.

41. In general, carriers of this type may be aqueous solutions comprising pharmaceutically acceptable cosolvents, such as for example, ethanol, polyethyleneglycol, propylenegylcol, glycerol and the like. Within this context, carriers of this type may be micellar solutions prepared with natural or synthetic ionic or nonionic surfactants. The carriers may also be combinations of these cosolvent, and micellar solutions.

EXAMPLE 2

Emulsion

42. In some cases, pharmaceutical preparations in the form of emulsions comprising special ingredients, detailed hereafter, may be advantageous.

43. These emulsions are prepared from an oily phase comprising pharmaceutically acceptable triglycerides, lecithine, stabilisers, antioxidants etc, in which phase the active compound is solubilized, and an aqueous phase containing glycerol and emulsifiers may optionally be added.

44. Preferred triglycerides are medium- and long-chain triglycerides. Deoxycholate is a preferred stabiliser. α-Tocopherol is a preferred anti-oxidant. Pluronic F-68, a non-ionic surfactant of a copolymer of polyoxyethylene and polyoxypropylene, is a preferred emulsifier.

45. Thus, a general example of as desired formulation of an "Emulsion" may be: triglycerides (from 1.0% to 30%, preferably 10%), lecithin (from 0.10% to 5%, preferably 1%), antioxidant, (% as required, according to the specific anti-oxidant used), stabiliser (from 0.05% to 5%, preferably 1%), glycerol (% as required for isotonicity), emulsifier (from 0.20% to 10%, preferably 2%), active compound (from 0.05% to 5%) and water up to 100% (all % w/w).

46. Preserving agents such as parabens may be added (0.01–0.1%).

47. A typical formulation (% w/w): 2-AG (5.0) stabilized in an oily phase (20.0), purified fractions egg yolk phospholipids (1.2), Pluronic F-68(2.0), glycerol (2–25), a-tocopherol (0.02), methyl-, butyl-p-hydroxybenzoic acid esters ((0.2) and (0.05), respectively) and bidistilled water (up to 100).

What is claimed is:

1. 2-Arachidonylglycerol (2-AG) to be used as an inhibitor of a tumor necrosis factor (TNF-α), used in the reduction of edema caused by closed head injury, used in the reduction of neurological deficits caused by closed head injury and stroke and used in treating pathological conditions caused by TNF-α and/or by radical oxygen intermediates (ROI).

2. A pharmaceutical composition comprising:

2-arachidonylglycerol (2-AG) as an active ingredient, wherein 2-arachidonylglycerol is used as an inhibitor for a tumor necrosis factor (TNF-α), is used in the reduction of edema caused by closed head injury, is used in the reduction of neurological deficits caused by closed head injury and stroke and is used in treating pathological conditions caused by TNF-α and/or by radical oxygen intermediates (ROI).

3. The pharmaceutical composition according to claim 2 comprising:

2-linoleoylglycerol (2-LinoG) and 2-palmitoylglycerol (2-PalmG) as additional active compounds.

4. The pharmaceutical composition according to claim 2 further comprising:

at least one of additional pharmaceutical active compounds and a suitable carrier, solvent, diluent or solid.

5. A method for the treatment of a tumor necrosis factor, edema, neurological deficits, stroke and for the treatment of pathological conditions caused by TNF-α and/or by radical oxygen intermediaries (ROI), said method comprising the step of:

administering one of:

2-arachidonylglycerol, a pharmaceutical composition comprising 2-arachidonylglycerol as an active ingredient, and a pharmaceutical composition comprising 2-arachidonylglycerol, 2-linoleoylglycerol (2-LinoG) and 2-palmitoylglycerol (2-PalmG) as active ingredients.

6. The method according to claim 5 wherein said administering comprises:

administering 0.05 mg to about 50 mg per kg body weight in regimen of 1–4 times a day.

7. The method according to claim 6 wherein a range of dosage for said administering is from 1.0 mg to about 20 mg per kg body weight.

8. 2-AG or pharmaceutical compositions comprising one of:

2-arachidonylglycerol, a pharmaceutical composition comprising 2-arachidonylglycerol as an active ingredient, and a pharmaceutical composition comprising 2-arachidonylglycerol, 2-linoleoylglycerol (2-LinoG) and 2-palmitoylglycerol (2-PalmG) as active ingredients, for the preparation of a medicament for the treatment of a tumor necrosis factor, edema, neurological deficits, stroke and for the treatment of pathalogical conditions caused by TNF-α and/or by radical oxygen intermediaries (ROI).

* * * * *